United States Patent [19]
Leverett

[11] Patent Number: 5,917,926
[45] Date of Patent: Jun. 29, 1999

[54] OPTICAL INSPECTION APPARATUS AND METHOD FOR ARTICLES SUCH AS FRUIT AND THE LIKE

[75] Inventor: William H. Leverett, Greenville, Ga.

[73] Assignee: Durand-Wayland, Inc., LaGrange, Ga.

[21] Appl. No.: 08/810,612

[22] Filed: Feb. 28, 1997

Related U.S. Application Data

[60] Provisional application No. 60/012,670, Mar. 1, 1996.

[51] Int. Cl.⁶ .................................................. G06K 9/00
[52] U.S. Cl. .......................... 382/110; 382/321; 209/585; 209/912
[58] Field of Search ...................................... 382/108, 110, 382/154, 318, 321, 324; 348/89, 91; 209/576, 577, 585, 912; 198/339.1, 469.1, 618, 620

[56] References Cited

U.S. PATENT DOCUMENTS

| | | | |
|---|---|---|---|
| 4,280,624 | 7/1981 | Ford | 209/524 |
| 4,411,366 | 10/1983 | De Greef | 209/648 |
| 4,482,061 | 11/1984 | Leverett | 209/592 |
| 4,645,080 | 2/1987 | Scopatz | 209/558 |
| 4,825,068 | 4/1989 | Suzuki et al. | 250/223 R |
| 5,251,266 | 10/1993 | Spigarelli et al. | 382/8 |

*Primary Examiner*—Andrew W. Johns
*Attorney, Agent, or Firm*—Jones & Askew

[57] ABSTRACT

Apparatus and method for optical inspection of fruit without rotating or otherwise repositioning the article during inspection. Plural mirrors are positioned to view different surface portions of each article moving along a path, and those mirrors consolidated the partial images to form a composite image viewable at a common objective such as a video camera. The images from individual mirrors are directed toward a pyramid having reflective surfaces, aiming those partial images toward the common objective aligned with the vertex of the pyramid. A holder supports each article above a conveyor with minimal surface contact, thereby minimizing portions of the article not visible for optical inspection.

10 Claims, 4 Drawing Sheets

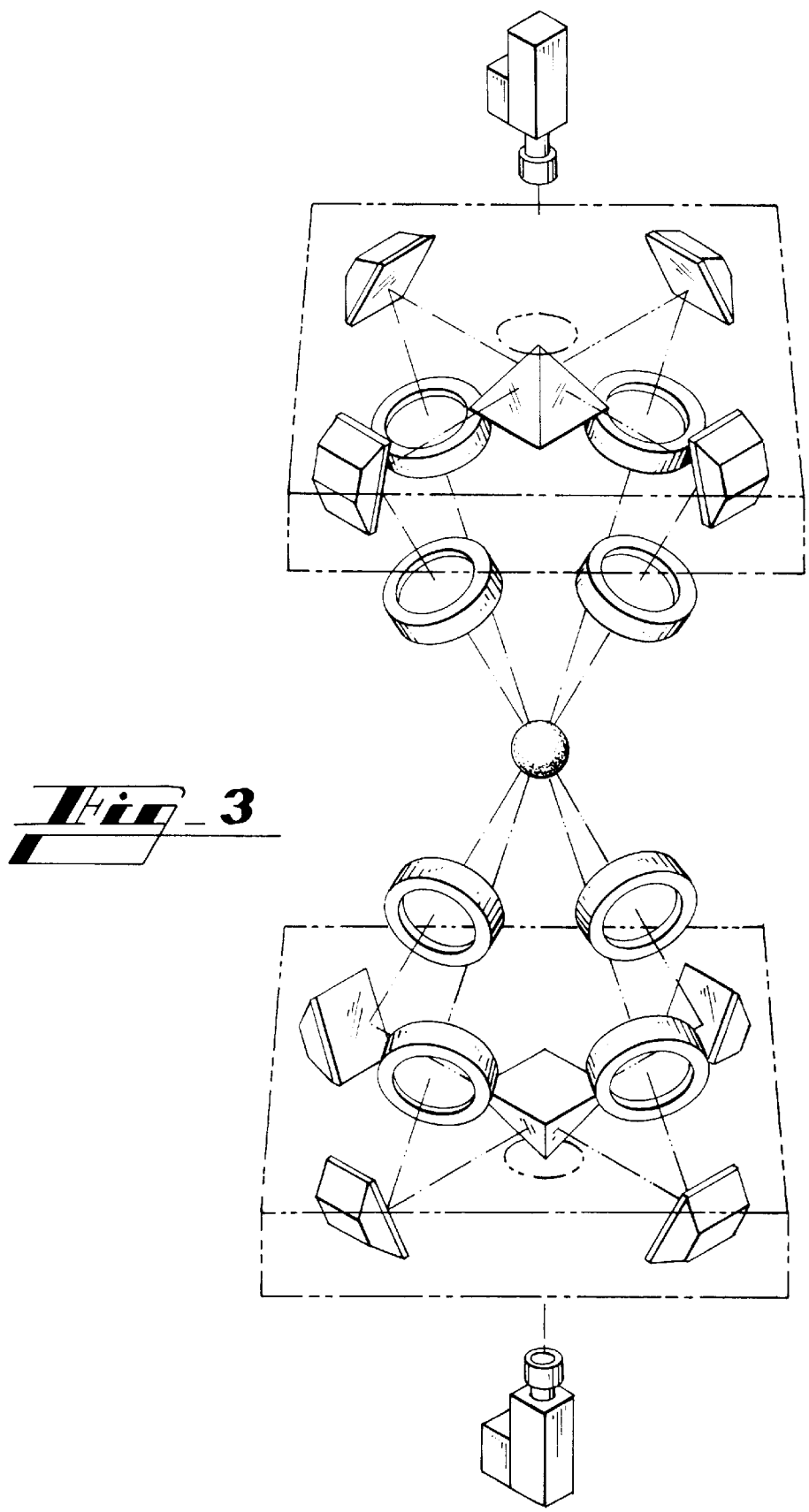
Fig_3

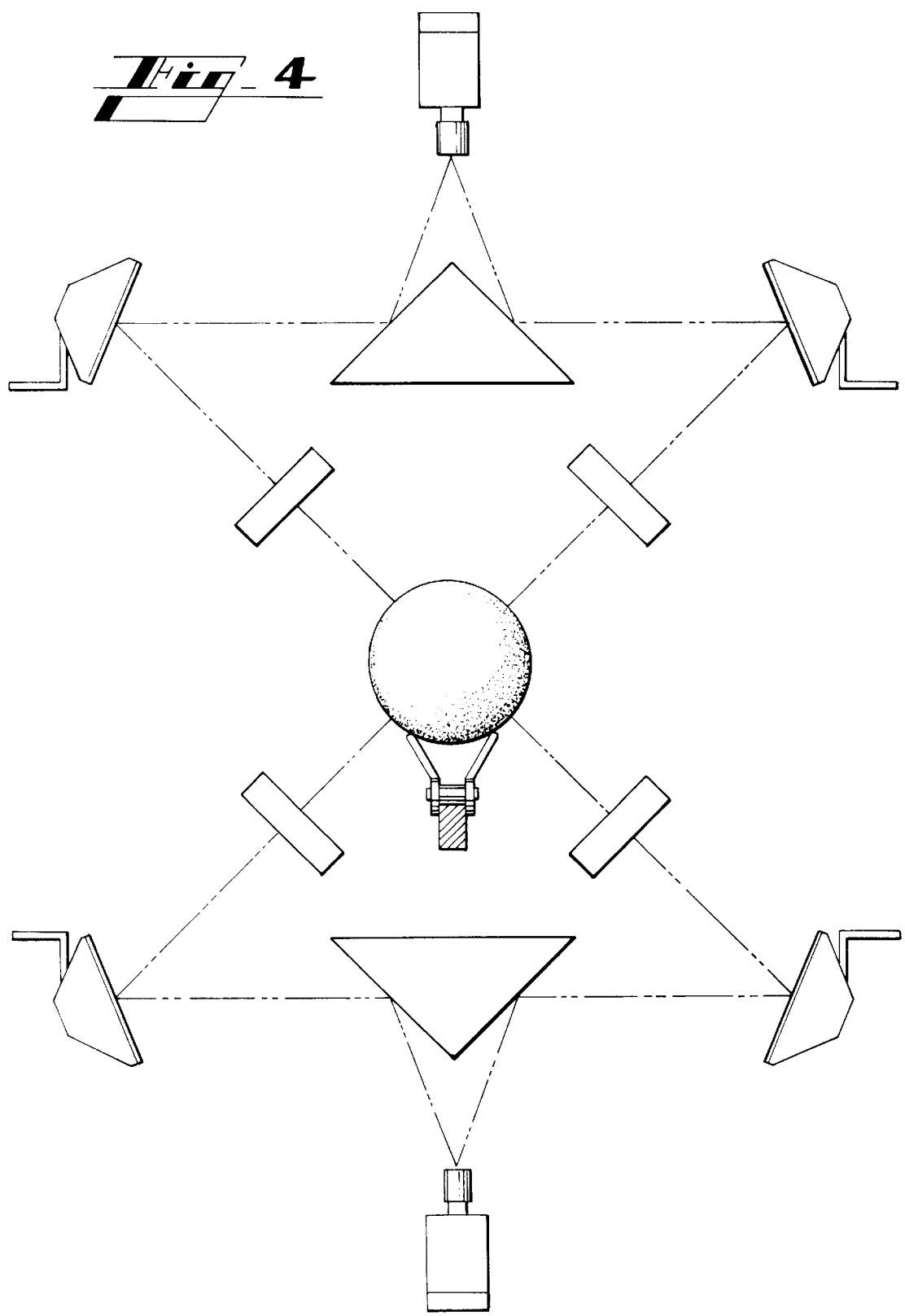
Fig_4

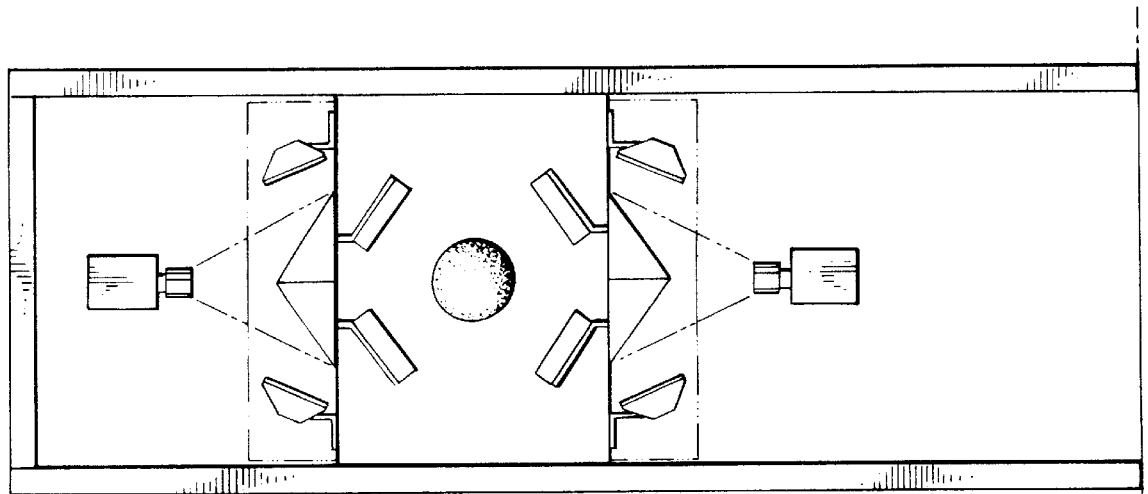
Fig_6
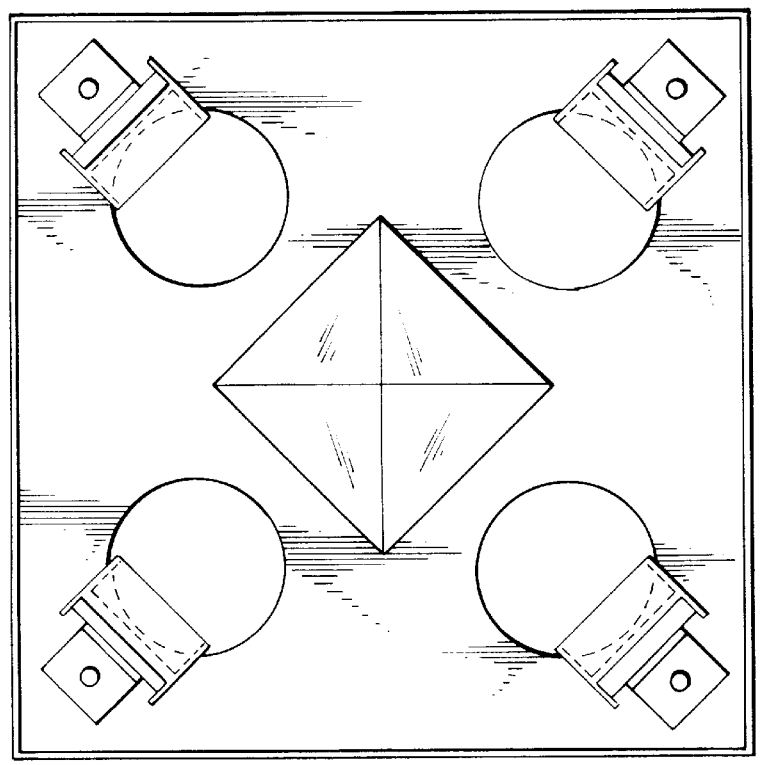
Fig_5

OPTICAL INSPECTION APPARATUS AND METHOD FOR ARTICLES SUCH AS FRUIT AND THE LIKE

CROSS-REFERENCE TO RELATED APPLICATION

This application claims the benefit of U.S. Provisional Application No. 60/012,670 filed Mar. 1, 1996.

FIELD OF INVENTION

This invention relates in general to inspecting articles, and relates in particular to an apparatus and method for optical inspection of articles such as fruit and the like to grade the articles.

BACKGROUND OF THE INVENTION

Articles of produce such as apples and citrus fruit usually are inspected as part of a commercial packing operation. This inspection may include viewing each article for color or other visual information indicating variable factors such as the degree of ripeness, the size or volume of the article, the shape of the article, and any blemishes or other local discolorations on the surface of the article. Articles such as grapefruit and oranges, for example, may be graded for sale as table-grade fruit, as suitable only for juicing, or to be thrown away as unacceptable, depending on the exterior appearance or other factors of each article.

Perhaps the simplest way to accomplish surface inspection of fruit is by human visual inspection of each article. The manpower requirements and resulting expense of human inspection for each article of fruit, the incompatibility of such inspection with the article throughput speeds available from other components of modern commercial packing house equipment, and the desire to grade each article to an objective standard, all emphasize the need for effective alternative solutions to the problem.

It has become known in the art to electronically scan articles such as fruit and to apply signal-processing techniques for evaluating the resulting scanned signals. For example, it is known in the art to position one or more video cameras that can scan articles of fruit and produce electronic signals corresponding to that scan. Those scanning signals are processed to provide information on factors such as the color, shape, or lack of uniform color of each article, as seen by the camera. Conventional video cameras or cameras utilizing photodiode arrays are proposed in the prior art for visual inspection of fruit. Various signal-processing algorithms or techniques can compare the measured signals for each article against predetermined signals corresponding to desired standards for the factors, thereby producing a objective grading standard for each inspected article.

The quality of grading produced by such optical inspection of fruit requires viewing substantially the entire surface of each article. For generally round articles such as grapefruit, successive articles are supported on rollers or wheels and conveyed single-file through an inspection station containing one or more video cameras. The rollers or wheels supporting each individual article are caused to rotate while conveying that article through the inspection station, in an effort to present all portions of the article by turning the article for scanning by the camera or cameras. However, a piece of fruit that is not round may slip as the rollers attempt to turn the piece, leaving part of the fruit unexposed to the camera.

Furthermore, the best results of such optical scanning are obtained by scanning each portion of the article substantially perpendicular to the boresight or optical axis of scan. For example, a single video camera positioned alongside a conveyor will see approximately one hemisphere of each grapefruit moving along that conveyor. However, the amount of usable information in the resulting video signal is best at the surface portions viewed head-on by the camera, that is, those portions at or nearly perpendicular to the optical axis of the camera. The quality of visual information obtained from that view becomes degraded due to optical foreshortening and imperfections at outer diameters of the camera lens, for portions of the fruit increasingly remote form the optical axis, i.e., near the outer regions of the hemisphere being viewed. Imperfections such as non-uniform color occurring near those outermost regions of view, may be missing from the video information produced by one or two cameras viewing an article moving between two opposed cameras, with the inspection techniques known in the prior art.

SUMMARY OF THE INVENTION

Stated in general terms, the present invention provides an apparatus and method for optical inspection of articles by concurrently viewing several different surface portions of the article to produce corresponding images of those different portions. The plural images are consolidated to form a composite image, and that composite image is evaluated to grade the article from which the images were produced.

Stated in somewhat greater detail, a number of optical elements are positioned relative to a predetermined path traveled by articles passing through an inspection region. Each optical element produces an image showing predetermined different portions of the article passing through that inspection region. The images from those optical elements pass along optical paths consolidating the images to a common objective. A scanning device such as a video camera or the like views the composite image at the common objective and converts that image to an electrical signal for subsequent processing. The optical elements used for scanning the individual portions of the articles comprise mirrors, in a preferred embodiment of the invention.

Stated in greater detail, an article inspection apparatus according to the present invention includes a number of reflectors mounted at one side of the path on which the articles travel. Each reflector is positioned to reflect an image from a different portion of an article passing through an inspection region. Those individual reflectors are mounted to reflect their respective images toward an arrangement of second mirrors, which in turn reflect those individual images toward a common objective such as the lens of a video camera. The second set of mirrors advantageously comprises mirrors in a pyramidal array, so that the individual images are reflected from the sides of the pyramid toward a video camera mounted in space relation to the vertex of the pyramid. Each reflective surface of the pyramid reflects the image from a corresponding one of the mirrors positioned to receive images of each article, so that the video camera aimed at the vertex of the pyramid will see a composite image of each such reflected image.

The reflectors in a particular application of the invention are advantageously positioned in quadrature with respect to one side of the inspection region, and reflect images from four quarters of the article or of one hemisphere thereof. A second set of scanning mirrors may be mounted in quadrature on an opposite side of the path traveled by the articles, scanning four different quadrants of the other hemisphere of each article. Each quadrature-related set of mirrors reflects its image to a different pyramid of reflectors, consolidating the images from each hemisphere into two separate composite images formed at two common objectives. Separate video cameras view the composite images at each common objective.

Because the present optical inspection apparatus and method can produce usable optical images of an entire article at the same time, there is no need to rotate or otherwise reposition the articles passing through the inspection region. Each article is supported on an article holder preferably having the smallest practical amount of structure engaging the article, so as to maximize the surface area of the article available for optical scanning. The article holder of the present invention thus has a number of article-contacting surfaces that preferably contact the article only at points tangent to the surface of the article. These support elements are located on a conveyor such as an endless chain or belt, and support each article above the conveyor as the articles are moved through the inspection region.

Accordingly, it is an object of the present invention to provide an improved apparatus and method for optical inspection of articles.

It is another object of the present invention to provide an apparatus and method for optical inspection of articles without rotating or otherwise repositioning the article during inspection.

It is a further object of the present invention to provide an apparatus and method for optical inspection of articles, while minimizing the effects of foreshortening or other image degradation and thus producing more usable information of the scanned image.

Other objects and advantages of the present invention will become more readily apparent from the following description of the preferred embodiment.

BRIEF DESCRIPTION OF DRAWINGS

FIG. 3 is an exploded perspective view showing the optical inspection zones of the preferred embodiment.

FIG. 4 is an enlarged schematic elevation view of the optical assembly shown in FIG. 3.

FIG. 5 is a top view of the optical inspection assembly in the preferred embodiment.

FIG. 6 is a front elevation view of the optical inspection apparatus in the preferred embodiment.

DETAILED DESCRIPTION OF PREFERRED EMBODIMENT

Figure 1:
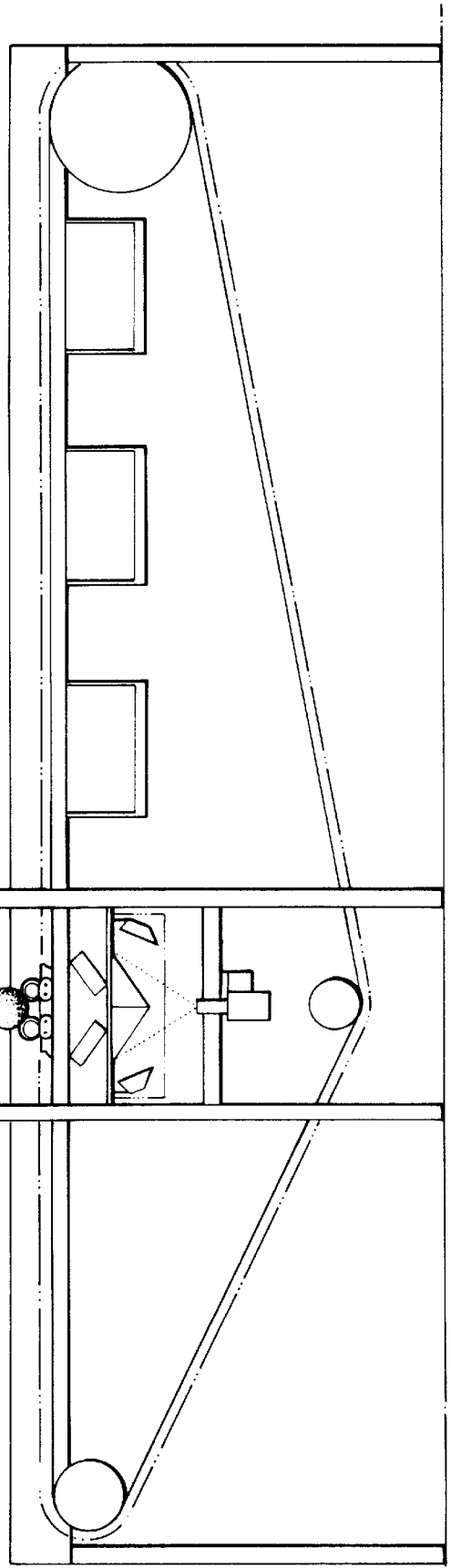
FIG. 1 is a side elevation view, partially broken away for illustrative purposes, showing an article inspection apparatus according to a preferred embodiment of the present invention.

Turning first to FIG. 1, there is shown generally at 10, an optical inspection apparatus according to a preferred embodiment of the invention. This apparatus includes a framework indicated generally at 11 and extending between an entrance end 12 and an exit end 13 of the inspection apparatus. The apparatus 10 in the preferred embodiment is intended for inspecting citrus fruit such as grapefruit or the like, as individual articles are moved single-file along a conveyor from the entrance 12 to the exit 13. Those articles thus pass through an inspection region 15 where optical viewing of each article takes place.

Articles are carried through the inspection apparatus 10 by a conveyor including an endless web 18 such as a chain or the equivalent, moving between a drive wheel 19 at the exit end of the apparatus and an idler wheel 20 at the inlet end. The return flight 21 of the conveyor chain is guided by a lower idler wheel 22 shown as located beneath the inspection region 15, although that idler wheel can be positioned elsewhere as appropriate.

Figure 2:
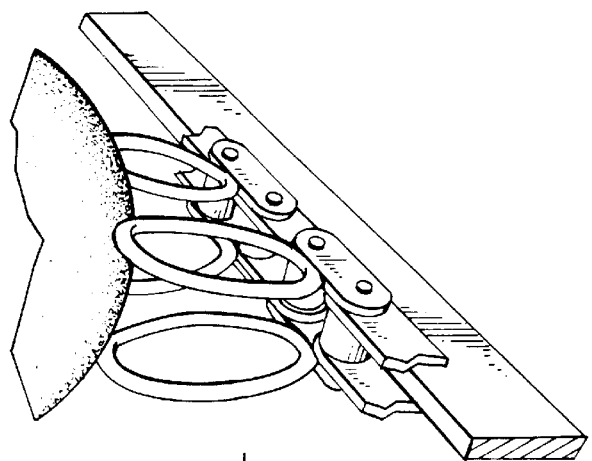
FIG. 2 is an enlarged perspective view showing an article holder according to the preferred embodiment.

Details of the conveyor web and one article holder are shown in FIG. 2. The conveyor comprises a drive chain moving along an elongated support rail 24 extending substantially the entire distance between the idler wheel 20 at the inlet end 12 and the drive wheel 19 at the exit 13. The drive chain itself is built up from a succession of separate interconnected links 25 having lower shoulders 26 that extend downwardly a distance below the top edge 27 of the rail 24. The shoulders 26 maintain the length in place on the rail 24 and promote stability of the conveyor chain as it moves along the rail. The rail 24 preferably is made of Teflon or covered by that material, or an equivalent material having relatively low sliding friction.

Although the conveyor in the disclosed embodiment is built up of individual chainlike links and thus is properly termed a conveyor chain, it should be understood that other forms of endless web conveyors, such as belts or cables, may be substituted for the chain used in the present embodiment. The term "chain" thus is used herein in a broader sense to encompass other forms of conveyor having an endless flexible web capable of carrying article holders on a closed path throughout the inspection apparatus.

Each article holder according to the present invention comprises a forward support element 31 mounted on and extending upwardly from a first set of links 32, and a rearward support element 34 likewise mounted on and extending upwardly from a second set of links 35. The terms "forward" and "rearward" are used with respect to the direction of travel by the conveyor along the rail 24. The forward support element 31 has a pair of generally circular ringlike members 38a and 38b attached at their lower sides to the first links 32 on opposite sides of the rail 24, and extending upwardly from the links. The ringlike members 38a and 38b are tilted outwardly a slight extent from vertical as shown in FIG. 4, so that the lateral spacing between the upper sides of the ringlike members is somewhat greater than the corresponding spacing between the links 32 at the lower ends of those members.

The second support element 34 likewise comprises a pair of ringlike members identical, in the disclosed embodiment, to the members 38a, 38b making up the first support element. The longitudinal distance between the first and second support elements 31 and 34 is chosen so that an article 40, such as a grapefruit, is supported in a relatively stable fashion when placed on the ringlike members of the first and second support elements. Each ringlike member 38a, 38b of both the forward support element 31 and rearward support element 34 contacts the article 40 substantially only at a point tangent to the surface of the article, so as to minimize the article surface area obscured to view by the article support. The open area within each ringlike member further promotes visual access to the article 40, both for illuminating that article and for viewing portions of the article as pointed out below in greater detail.

Details of the inspection region 15 are best understood by referring to FIGS. 3 and 4 in light of the following description. The two video cameras 44 and 45, respectively mounted at upper and lower portions of the frame assembly 46 straddling the endless web 18 and the rail 24 of the article conveyor, together view composite images that encompass substantially the entire surface area of each article 40 moving through the inspection region. This viewing takes place by means of upper and lower optical inspection zones 49 and 50 spaced apart from each other on opposite sides of the path traveled by each article 40. As best seen in FIG. 3, the inspection zone 49 is located above the path 48 traveled by the articles and the inspection zone 50 is located below that path.

Considering first the upper optical inspection zone 49, that zone includes a housing 56 shown in outline in FIG. 3 and omitted from FIG. 6 for clarity, supporting four mirrors 57 mounted at the respective four corners of the housing. Each mirror 57 is mounted behind a corresponding opening 58 in the bottom plate 59 (FIG. 5) of the housing 53. The mirrors 57 and openings 58 are positioned with respect to the article conveyor so that each mirror reflects a partial image of an article 40 passing through the inspection region 15. Because the mirrors 57 are four in number in the preferred embodiment and are arranged in quadrature within the housing 56 located above the article 40, each such mirror views substantially a quadrant of the upper hemisphere of each article positioned directly below the upper optical inspection zone 49 while moving through that zone.

The four mirrors 57 are positioned within the upper housing 56 at equal distances from confronting reflective surfaces of a right pyramid 63 whose base is supported on the bottom plate 59 of the upper housing. Each upper-quadrant partial image of the article 40 thus passes along an optical path 65 (FIG. 4) and through one of the openings 58 in the bottom plate 59 to impinge a corresponding one of the mirrors 57. That image is reflected along a second optical path 67 from the mirror 57 to a confronting reflective surface 66 forming one side of the pyramid 63, which reflects the image along the optical path 70 to the lens of the video camera 44 associated with the upper optical inspection zone 49. The camera 44 preferably is positioned such that its optical bore sight is directly above the vertex 72 of the pyramid 63, along an imaginary line entering that vertex and normal to the base of that right triangle.

It should now be apparent that as the image from one upper quadrant of the article 40 is seen by the camera 44 as reflected off the face 66 of the pyramid, images from the three remaining upper quadrants of that article simultaneously are reflected from the other three mirrors 57 and the corresponding three other sides of the pyramid 63. The placement of the four mirrors 57 and the reflective surfaces of the pyramid 63 thus consolidate the partial images from the upper quadrant of the article 40, and the camera 44 sees those consolidated images at a common objective, namely, the camera lens, which focuses the consolidated images onto the active elements of the camera. The video camera 44 thus produces a video output signal containing visual information corresponding to the entire upper quadrant of the article 40. Because the optical path 65 extending from the article to each mirror 57 is perpendicular to the surface at a corresponding upper quadrant of the article, the amount of image distortion due to foreshortening is greatly reduced for each quadrant image, relative to simply viewing the entire upper half of the article through a video camera aimed at that article.

Each upper quadrant of the article 40 preferably is separately illuminated to reduce shadowing and to provide uniform color balance for the images reflected from those quadrants to the video camera. This illumination is accomplished in the preferred embodiment by means of the four circular lighting fixtures 76, best seen in FIG. 2. Each lighting fixture comprises a ringlike housing surrounding an open region, and an illumination source mounted within that housing to direct illumination downwardly from the lighting fixture toward a point occupied by each article 40 at a predetermined point while traveling through the inspection region 15. Each ringlike lighting fixture 76 is aligned so that the corresponding optical path 65 from the article to the mirror 57 passes through substantially the open interior 77 of the hollow ringlike housing, so that the lighting fixtures do not interfere with the reflected images from the article. The four lighting fixtures 76 are mounted on a bracket fastened to the underside 78 of the bottom plate 59, so that the longitudinal axis of each lighting fixture is substantially coaxial with the optical path 65 extending there through.

The upper housing 50 is closed by an upper plate 79 to protect the mirrors 57 and the reflective pyramid 66 from exposure to dirt or objects that could misalign or damage the optical paths. A central opening 80 in the upper plate 79 is sized to permit the upper video camera 44 to see the pyramid 63 and the images reflected from all four faces 69 of that pyramid.

The lower optical inspection zone 50 is essentially an inverted duplication of the upper optical inspection zone 49. As best seen in FIG. 1, the lower inspection zone 50 is positioned a distance below the conveyor rail 24 and directly beneath the upper optical inspection zone 49. The lower inspection zone 50 includes four mirrors positioned in a quadrature relation within a lower housing 84 to reflect images from respective quadrants along the lower hemisphere of each article 40 passing through the inspection region. The images from each mirror 83 are aimed toward reflective faces 85 on the lower pyramid 86, so that those quadrature images are consolidated for viewing by the lower video camera 45. Separate lighting fixtures 88 are mounted above the top surface 89 of the lower housing 84 to illuminate the four lower quadrants of each article 44, in the same manner as the lighting fixtures 76 described above.

The operation of the preferred embodiment should now be apparent from the foregoing description. As each article 40 passes through the inspection region, each video camera 49 and 50 simultaneously sees four quadrant images reflected from the pyramid faces by means of the mirrors 57, 83 reflecting images onto those faces. Each video camera thus sees a composite image comprising the four quadrants from the respective upper and lower hemispheres of the article. Each reflected image is a straight-on view from a particular quadrant of the article, and so those images are relatively undistorted in contrast with prior art imaging devices wherein a single camera produced an optical image of an entire half of an article such as a citrus fruit or the like.

The processing of image signals from the video cameras is known to those skilled in the art and is not discussed herein in detail. For example, conventional frame grabbers (not shown) are operated to capture the video signals from each camera, at the time each article 40 passes a predetermined location between the upper and lower inspection zones. Those video signals then are processed by techniques known in the art to evaluate factors such as color, size, and shape of each article, and the individual articles are graded according to those factors. Each article may be automatically ejected into one of the bins 90, 91, and 92 located downstream from the inspection region 15, depending on appropriate grading of those qualities. The highest-graded articles may also pass beyond the exit 13 of the inspection apparatus for further processing or packing. Apparatus for selectively ejecting articles of fruit from the conveyor into the appropriate bin is known to those skilled in the art and thus is not discussed herein.

It should be understood that the foregoing relates only to a preferred embodiment of the present invention and that numerous changes and modifications thereto may be made without departing from the spirit and scope of the invention as defined in the following claims.

I claim:

1. An apparatus for the inspection of articles, comprising:
   a conveyor operative to move articles along a predetermined path including an inspection region;
   a plurality of imaging elements positioned with respect to the inspection region so that each imaging element views only a portion of an article therein and produces an image of the respective portion;
   optical means receiving the separate images produced by the imaging elements and directing those separate images to form a composite image at a common objective;
   a video camera responsive to the composite image at the common objective so as to view the composite separate images of the article, so that the video camera can produce an output signal corresponding to portion viewed by the plural imaging elements;
   the imaging elements comprising a first plurality of reflectors arrayed at one side of the path on which the articles travel, and a second plurality of reflectors arrayed at another side of said path;
   each reflector of the first plurality is positioned to reflect an image from a different portion of a first predetermined spatial region of the article, and each reflector of the second plurality is positioned to reflect an image from a different portion of a second predetermined spatial region of the article;
   the optical means comprises a first optical means receiving the separate images reflected from the first plurality of reflectors and directing those separate images to a first common objective, and a second optical means receiving the separate images reflected from the second plurality of reflectors and directing those separate images to a second common objective; and
   the video camera is one of two such cameras, each camera separately viewing the respective common objectives, so that the video cameras together produce output signals corresponding to all portions of the first and second spatial regions viewed by the reflectors.

2. Apparatus as in claim 1, wherein:
   each plurality of reflectors comprises reflectors positioned in quadrature with respect to the inspection region and on mutually opposite sides of that region, so that the first plurality of reflectors reflects images from respective quadrants of one hemisphere of the article and the second plurality of reflectors reflects images form respective quadrants of another hemisphere of the article.

3. An apparatus for the inspection of articles, comprising:
   a conveyor operative to move articles along a predetermined path including an inspection region;
   a first plurality of reflectors arrayed at one side of the path on which the articles travel, the reflectors of the first plurality positioned to reflect respective images from different portions of a first predetermined spatial region of the article;
   a second plurality of reflectors arrayed at another side of said path, the reflectors of the second plurality positioned to reflect respective images from different portions of a second predetermined spatial region of the article;
   a plurality of reflective surfaces comprising surfaces of a pyramid, with each reflective surface receiving a separate image produced by a corresponding reflector of the first and second pluralities of reflectors and the reflective surfaces directing those separate images to form a composite image at a common objective aligned with the vertex of the pyramid; and
   a video camera responsive to the composite image at the common objective so as to view the composite separate images of the article,
   so that the video camera can produce an output signal corresponding to the portions viewed by the plural reflectors.

4. Apparatus as in claim 3, wherein:
   each reflector views the respective image along a predetermined image path; and further comprising
   a source of illumination substantially encircling each predetermined image path and directing illumination toward the portion of the article viewed on that image path.

5. Apparatus for optical inspection of articles, comprising:
   a conveyor comprising an endless chain operative to move articles along a predetermined path including an inspection region;
   first and second pairs of ringlike members carried by the chain in longitudinal separation;
   the ringlike members of each pair being attached at lower portions to the chain in mutually lateral separation and each extending upwardly from the lower portion to an upper portion for supporting an article;
   an open area within each ringlike member through which a portion of the article being supported is visible for inspection;
   a plurality of imaging elements positioned with respect to the inspection region so that each imaging element views only a portion of an article therein and produces an image of the respective portion;
   optical means receiving the separate images produced by the imaging elements and directing those separate images to form a composite image at a common objective; and
   a video camera responsive to the composite image at the common objective so as to view the composite separate images of the article,
   so that the video camera can produce an output signal corresponding to portions viewed by the plural imaging elements.

6. Apparatus as in claim 5, wherein:
   each imaging element comprises a mirror positioned to view a respective different portion of an article in the inspection region.

7. Apparatus as in claim 6, wherein:
   each mirror reflects a partial image of the article as viewed along a predetermined optical path between the mirror and the corresponding portion of the article; and further comprising
   separate illumination sources positioned between the respective mirrors and portions of the article, and operative to illuminate said positions for reflection in the mirrors without shadows.

8. Apparatus as in claim 6, wherein each illumination source at least partially surrounds a respective optical path between the mirror and the article.

9. Apparatus as in claim 5, wherein:
the imaging elements comprise mirrors positioned in quadrature with respect to the inspection region and operative to reflect corresponding partial images of an article in the inspection region.

10. An article holder for supporting an article for movement by an endless web movable along a predetermined path containing imaging elements, the holder comprising:

first and second pairs of ringlike members carried by and extending above the endless web to contact respective first and second surface locations on the article;

the second pair being spaced apart from the first pair along the predetermined path so that the ringlike members contact a lower region of the article at points spaced apart on the article and thereby support the article above the web;

the ringlike members of each pair being attached to the web in mutually lateral separation at lower portions and extending upwardly from the web to upper surfaces mutually spaced apart in a direction transverse to the predetermined path, so that each ringlike member contacts the article surface substantially only at respective location points tangent to the surface of the article and the surface of the article is substantially out of contact with the article holder elsewhere except for the tangent points;

an open area within each ringlike member through which a lower portion of the article being supported is visible for inspection;

so that leaving the surface of the article, except for the tangent points, remains substantially unobstructed by the article holder for viewing by the imaging elements.

* * * * *